United States Patent [19]
Lee

[11] 3,956,163
[45] May 11, 1976

[54] PIGMENTED DETERGENTS

[75] Inventor: Do Ik Lee, Midland, Mich.

[73] Assignee: The Dow Chemical Company, Midland, Mich.

[22] Filed: Aug. 20, 1973

[21] Appl. No.: 389,746

[52] U.S. Cl. .......................... 252/171; 252/DIG. 2; 252/DIG. 14; 252/DIG. 15; 260/29.6 ME; 260/29.6 PM
[51] Int. Cl.² ........................................ C11D 1/83
[58] Field of Search ................ 252/DIG. 2, DIG. 1, 252/DIG. 15, DIG. 14, 171, 104; 260/29.6 E, 29.6 ME, 29.6 PM, 29.6 XA

[56] References Cited
UNITED STATES PATENTS

| | | | |
|---|---|---|---|
| 2,840,549 | 6/1958 | McNulty | 260/80 |
| 2,892,802 | 6/1959 | Budewitz | 260/29.6 ME |
| 3,060,139 | 10/1962 | Greminger | 260/17 |
| 3,244,658 | 4/1966 | Grosser | 260/29.6 E |
| 3,297,621 | 1/1967 | Taft | 260/29.6 ME |
| 3,301,806 | 1/1967 | Guziak | 260/29.6 ME |
| 3,321,408 | 5/1967 | Briggs | 252/161 |
| 3,442,844 | 4/1969 | Bouchard | 260/29.6 T |
| 3,506,602 | 4/1970 | Floros | 260/29.6 T |
| 3,595,823 | 7/1971 | Huang | 260/29.6 T |
| 3,844,990 | 10/1974 | Lindemann | 260/17 R |

FOREIGN PATENTS OR APPLICATIONS 848,497   8/1970   Canada

Primary Examiner—Samuel W. Engle
Assistant Examiner—Ralph Palo
Attorney, Agent, or Firm—R. G. Waterman; M. S. Jenkins

[57] ABSTRACT

Pigmented detergents having improved shelf stability are provided by dispersing in liquid detergent a polymeric pigment made by an emulsion polymerization process comprising the steps of (1) emulsion polymerizing from about 0 to about 80 weight percent of total monomer in absence of emulsifier, (2) adding a nonionic surfactant, and (3) continuing emulsion polymerization of the remaining monomer charge.

10 Claims, No Drawings

PIGMENTED DETERGENTS

BACKGROUND OF THE INVENTION

This invention relates to pigmented liquid detergent having colloidal size plastic particles as pigment.

It is known that clear liquid detergents, hair creams, floor waxes, etc., which are maintained at an alkaline pH can be opacified by adding certain polymeric latices thereto, that the opacified detergents have a milky, smooth appearance which is generally regarded as aesthetically superior to the appearance of clear detergents, and that best results in opacifying the detergents are obtained when the polymeric latices have an average particle size generally larger than conventional latex particle size. Unfortunately, difficulties have been encountered in achieving efficient opacification of such detergents, etc., because polymeric latices having a large particle size are time-consuming to make and are usually unstable in these detergents.

Therefore, it would be highly desirable to provide a pigmented detergent containing as pigment a polymeric latex having large average particle size which is stable in a wide variety of detergents.

SUMMARY OF THE INVENTION

In accordance with the present invention, there is provided a novel, improved pigmented detergent having good shelf stability. The improvement achieved in the practice of this invention results from the combination of an aqueous detergent and an opacifying amount of a latex of an emulsion polymer which is prepared by a modified emulsion polymerization process. The emulsion polymer is further characterized as being non-film forming and water- and detergent-insoluble. This process comprises the steps of (1) subjecting a polymerization recipe containing an aqueous medium, a catalyst and an incrementally added emulsion polymerizable monomer to conditions of emulsion polymerization; (2) adding an excess of nonionic surfactant to the polymerization recipe when from 0 to about 80 weight percent of total monomer has been polymerized; and (3) continuing addition and emulsion polymerization of remaining monomer.

The improved pigmented detergents of this invention exhibit surprising shelf stability over substantial periods of time. Such surprising shelf stability is believed to be attributable to the strong bonding of the nonionic surfactant onto the surface of the latex particle surfaces during polymerization. The bond between the nonionic surfactant and latex particle is believed to remain intact even after the polymeric latex is dispersed in the aqueous detergent.

The practice of the invention is useful in opacification of aqueous detergent compositions such as liquid detergents, hair creams, facial preparations, floor wax and numerous other similar liquid or semi-liquid compositions.

DESCRIPTION OF THE PREFERRED EMBODIMENTS

The discrete particles useful as the polymeric pigment are composed of any non-film forming organic polymer which is water-insoluble and is insoluble in the particular detergent to be pigmented. Preferred polymers are thermoplastic, organic, resinous materials which are substantially colorless.

By "non-film forming," it is meant that the dispersed polymeric pigment does not coalesce to form a film at ambient temperature or at temperatures to which the detergent will normally be exposed during storage prior to use. If the discrete polymeric particles throughout the detergent fuse or coalesce prior to use, the opacity of the detergent will be reduced substantially. Accordingly, it is necessary to use polymeric particles which are not dissolved or softened by the particular detergent to be pigmented.

In preparation of the polymeric pigment, any monomer or mixture of monomers can be used which is polymerizable under conditions of aqueous emulsion polymerization and which forms a polymer having the specified physical properties of being water-insoluble and non-film forming. Preferred emulsion polymerizable monomers which can be polymerized and/or copolymerized with each other in any proportions and/or with other monomers as specified hereinafter to yield such polymers include ethylenically unsaturated monomers such as the monovinylidene carbocyclic aromatic monomers, e.g., styrene, α-methylstyrene, ar-(t-butyl)styrene, ar-methylstyrene, ar,ar-dimethylstyrene, ar-chlorostyrene, ar-(t-amyl)styrene, ar-bromostyrene, ar-fluorostyrene, ar-cyanostyrene, ar-methoxystyrene, ar-ethylstyrene, ar-hydroxymethylstyrene, ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of $\alpha,\beta$-ethylenically unsaturated carboxylic acids which polymerize to form non-film forming polymers, e.g., methyl methacrylate, chloroethyl methacrylate, 2-butyl methacrylate, 3,3-dimethylbutyl methacrylate, 3,3-dimethyl-2-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters wherein the alkyl moiety has from 1 to 20 carbon atoms and the acid moiety has from 3 to 8 carbon atoms; $\alpha,\beta$-ethylenically unsaturated esters of non-polymerizable carboxylic acids, e.g., vinyl benzoate, vinyl ar-toluate, vinyl ar-ethylbenzoate, allyl ar-ethylbenzoate, vinyl trimethylacetate, vinyl pivilate, vinyl trichloroacetate and other such monomers wherein the unsaturated moiety has from 2 to 14 carbon atoms and the acid moiety has from 2 to 12 carbon atoms; $\alpha,\beta$-ethylenically unsaturated nitriles, e.g., acrylonitrile, methacrylonitrile, fumaronitrile and other such nitriles having not more than 12 carbon atoms; other polymerizable vinyl monomers such as vinyl chloride, vinyl bromide and the like.

The foregoing monomers are generally classified as hard monomers as they polymerize or copolymerize with each other to form non-film forming polymers as required in the practice of this invention.

Lesser amounts, such as less than about 45 weight percent based on the polymer, of other ethylenically unsaturated monomers which normally polymerize to form film-forming polymers (so-called soft monomers) are suitably copolymerized with the foregoing hard monomers. Examples of such monomers include conjugated aliphatic dienes such as 1,3-butadiene, isoprene, 2-chloro-1,3-butadiene and other such dienes having not more than 14 carbon atoms; alkyl acrylates such as methyl acrylate, ethyl acrylate, propyl acrylate, n-butyl acrylate, isobutyl acrylate, amyl acrylate, lauryl acrylate, isoamyl acrylate, 2-ethylhexyl acrylate, octyl acrylate, and other such acrylates having alkyl moieties of not more than 18 carbon atoms; unsaturated esters of saturated carboxylic acids such as vinyl acetate, vinyl propionate, vinyl butyrate, allyl acetate and other such esters having not more than 18 carbon atoms; esters and half esters of $\alpha,\beta$-ethylenically unsaturated polycarboxylic acids, e.g., dimethyl fumarate, diethyl maleate, methyl ethyl fumarate, ethyl hydrogen maleate, dioctyl fumarate and the like; other copolymerizable ethylenically unsaturated monomers such as vinyl fluoride, vinylidene chloride and vinylidene fluoride. Maximum concentrations of these monomers are governed primarily by the temperature to be reached by the detergent prior to use and the degree to which a particular monomer lowers the softening point of the resulting copolymer. For illustration, if a copolymer of styrene and butadiene is to be used as the polymeric pigment, butadiene normally is not present in the copolymer in amount more than about 20 weight percent. If, however, the styrene/butadiene copolymer has more than the normal amount of crosslinking, butadiene may be present in concentration greater than 20 weight percent with the maximum concentration of butadiene being dependent on the actual degree of crosslinking. Increased crosslinking is usually promoted by irradiation or by use of a suitable crosslinking agent such as unsaturated polyester or polyethylenically unsaturated monomer. Exemplary polyethylenically unsaturated monomers include divinyl benzene, trivinyl benzene, divinyl naphthalene, and the like. In regard to the use of the aforementioned soft monomers, use in any concentration is suitable provided that the resultant polymer is non-film forming as required in the practice of this invention.

In addition to the foregoing monomers, other monomers which may also be copolymerized constituents of the polymeric pigment are $\alpha,\beta$-ethylenically unsaturated carboxylic acids including both mono- and polycarboxylic, e.g., dicarboxylic acids, such as acrylic acid, methacrylic acid, itaconic acid, fumaric acid, maleic acid and anhydride, citraconic acid and anhydride and other such acids. Maximum concentrations of these acid comonomers in the polymeric pigment are limited by the degree to which they promote water solubility of the polymer. Since the polymeric pigment is required to be water-insoluble, the acid comonomers are generally employed in concentrations not greater than 25 weight percent of the polymeric pigment.

Preferred polymers used in the polymeric pigment are copolymers of from about 40 to about 99 weight percent of one or more of the aforementioned hard monomers, from about 0 to about 45 weight percent of one or more of the aforementioned soft monomers and from about 1 to about 15 weight percent of one or more emulsion copolymerizable $\alpha,\beta$-ethylenically unsaturated carboxylic acids, preferably those having 3 to 8 carbon atoms. Especially preferred copolymers are copolymers of from about 50 to about 99 weight percent of monovinylidene carbocyclic aromatic monomers such as styrene and ar-(t-butyl)styrene, from about 0 to about 49 weight percent of $\alpha,\beta$-ethylenically unsaturated nitrile such as acrylonitrile and methacrylonitrile, and from about 1 to about 5 weight percent of $\alpha,\beta$-ethylenically unsaturated carboxylic acid such as acrylic acid, methacrylic acid and itaconic acid. Examples of such especially preferred copolymers are styrene/acrylic acid copolymers, styrene/acrylonitrile/itaconic acid copolymers, styrene/methacrylic acid copolymers, vinyl benzoate/acrylic acid copolymers, t-butyl styrene/acrylonitrile/acrylic acid copolymers and vinyl chloride/acrylic acid copolymers. In the foregoing preferred copolymers, it is sometimes beneficial to copolymerize from about 0.5 to about 15 weight percent of polyethylenically unsaturated monomer such as divinyl benzene therewith.

The specific gravity of the preferred polymers used in the practice of the invention usually is within the range of about 0.9 to about 1.4 g/cc. It is preferable that the particles be made from a polymer which is predominantly hydrocarbon since such polymers have a specific gravity generally less than about 1.4. The refractive index of preferred polymers is generally in the range of from about 1.2 to about 1.7, especially from about 1.4 to about 1.6.

In addition to being composed of discrete particles of non-film forming polymer as set forth hereinbefore, it is preferred that the polymeric pigment be in the form of particles having an average diameter in the range of from about 0.2 to about 2 microns, with no more than about 5 weight percent of the particles based on total weight of particles forming the polymeric pigment having diameters outside said range, preferably not more than 3 weight percent. The preferred embodiment of the method described herein is capable of producing such polymeric particles. In addition, this method usually produces particles which have essentially rough surfaces as observed with an electron transmission microscope. Also, the method produces bimodal, or even trimodal, aqueous dispersions of polymeric particles wherein most of the polymer is in the form of particles having diameters in the range specified hereinbefore and a minor amount, e.g., not more than about 5 percent, is in the form of particles having diameters in the range of from about 0.03 to about 0.15 micron. It has been observed that the practice of the method of this invention using any given monomer system yields an aqueous dispersion of polymeric particles having improved stability when dispersed in detergent as compared to detergents containing aqueous dispersions made using a conventional emulsion polymerization process.

The polymeric pigment as described hereinbefore is advantageously prepared by an improved emulsion polymerization process as broadly set forth hereinbefore wherein at least about 20 weight percent of total monomer is polymerized in the presence of nonionic surfactant. More specifically, the improved emulsion polymerization process of this invention is preferably prepared in a batchwise manner indicated as follows. The polymerization zone is preferably purged with inert gas, charged with a water-soluble polymerization catalyst and water, and brought to a suitable reaction temperature. The amounts of water and catalyst initially charged to the polymerization zone are those typically employed in conventional emulsion polymerization carried out by continuous feeding of monomer during polymerization. Preferably, the amount of catalyst charged is from about 0.1 to about 1 weight percent based on total monomer and the amount of water charged is from about 50 to about 150 weight percent based on total monomer.

It is understood, however, that it is within the scope of this improved process to charge the polymerization zone with additional amounts of catalyst and water during polymerization, in fact, it is sometimes advantageous to do so and also to add basic materials such as ammonium hydroxide or alkali metal hydroxide in order to enhance stability of the latex. It is further understood that catalyst can be added continuously, separately or with the monomer feed stream. In addition, activators such as a sulfoxylate activator can be added intermittantly or continuously to the polymerization zone in so-called "redox-catalyzed" polymerization.

As polymerization catalysts, there may be used one or more peroxides which are known to act as free-radical catalysts. Usually convenient are the persulfates (including ammonium, sodium, and potassium persulfates), hydrogen peroxide, or the perborates or percarbonates. There may also be used organic peroxides, either alone or in addition to inorganic peroxide or sulfoxylate compounds. Typical organic peroxides include benzoyl peroxide, tert-butyl hydroperoxide, cumene peroxide, acetyl peroxide, caproyl peroxide, tert-butyl perbenzoate, tert-butyl diperphthalate, methyl ethyl ketone peroxide, and the like.

The choice of an inorganic or organic peroxide catalyst depends in part upon the particular combination of monomers to be polymerized. As might be expected, some of the monomers respond better to one type of catalyst than the other. The usual amount of catalyst required is approximately from about 0.01 percent to about 3.0 percent by weight as based on the weight of the total monomer charge.

In some instances, in order to effect polymerization at a temperature below that at which coagulation of the latex might occur, it may be desirable to activate the catalyst. The activation may be best accomplished by using a redox system in which a reducing agent within the limits of about 0.001 percent to about 6 percent as based on the weight of total monomers is present in addition to the peroxide catalyst. Many examples of such redox systems are known. Agents, such as hydrazine or a soluble oxidizable sulfoxy compound, including the alkali metal salts of hydrosulfites, sulfites, and bisulfites, and the like can be employed. Redox systems may be activated by the presence of a small amount (a few parts per million) of polyvalent metal ions. Ferrous ions are commonly and effectively used or a tertiary amine which is soluble in the reaction medium may also be used as an activator.

Continuous feeding of the total monomer is begun after water and catalyst have been charged or simultaneous therewith. The polymerization zone is brought to desired polymerization temperature which is advantageously in the range of from about 30° to about 98°C, preferably from about 70° to about 98°C, prior to beginning of monomer feed or shortly thereafter. Generally, aqueous dispersions of polymeric particles having better coating properties are produced at the higher temperatures within the aforementioned range. The rate of monomer feed is not particularly critical; however, it is generally desirable to feed at a rate such that addition of total monomer charge will be complete in a period from about 2 to about 24 hours, preferably from about 4 to about 6 hours. It is preferred, but not critical, to stop the monomer feed after about 15 to about 70 weight percent of the total monomer has been added and the mixture is allowed to digest for about 5 to about 60 minutes before resuming addition of the initial portion of the total monomer charge. This digestion period will hereinafter be referred to as an "initial stage digestion." Such practice usually provides a very mild exotherm in the polymerization, which otherwise, with some monomers, will occur at an unpredictable time and be quite vigorous. Employment of this advantageous step also reduces the amount of coagulum by-product which is often produced.

While the emulsion polymerization of the total monomer in accordance with this invention can begin in the presence of the nonionic surfactant, it is preferred to polymerize an initial portion of total monomer constituting from about 15 to about 70 weight percent of total monomer charge in the absence of the nonionic surfactant or any other emulsifier. It is found that this practice of polymerizing an initial portion of monomer in the absence of emulsifier facilitates the production of larger particle size latexes, e.g., average particle diameter generally in the range from about 0.2 to about 2 microns, which are more efficient as opacifiers.

It is critical, however, in the practice of this invention that polymerization of at least about 20 weight percent of total monomer be carried out in the presence of nonionic surfactant. It is understood that nonionic surfactant includes a single nonionic surfactant and mixtures of two or more nonionic surfactants. In combination with the nonionic surfactant, there may be employed anionic surfactants. Thus, for the purposes of this invention, the term "emulsifier" includes both nonionic and anionic surfactants, and specifically excludes polymerization catalysts and monomeric materials as defined hereinbefore.

During the preferred substantially emulsifier-free stage of the polymerization reaction, it is preferably to permit polymerization to proceed without addition of further ingredients to the polymerization other than addition of catalyst and, if desired, base and/or activator, for a period of from about 1 to about 8 hours to avoid buildup of reactants. After the initial portion of monomer has been added and polymerization thereof is essentially complete, nonionic surfactant or combination thereof with anionic surfactant is added to the polymerization recipe. It is required to add an excess of nonionic surfactant. By "an excess" of nonionic surfactant is meant an amount more than that required to completely cover the total surface area of the latex polymer particles such that new polymerization sites are provided by the excess nonionic surfactant. Relationship of surface area of latex particles to emulsifier concentration is set forth in D. C. Blackley, High Polymer Latices, Vol. 2, 486–491 (1966). The amounts of nonionic surfactant required to provide an excess depend primarily on the concentration of monomers to be handled and, to a further extent, with the choice of nonionic surfactant, type and concentration of other emulsifier such as anionic surfactant, and proportions of monomers. As a general rule, from about 2 to about 10 weight percent of nonionic surfactant based on total monomer is an advantageous amount, with from about 2 to about 4 weight percent being preferred.

Emulsifiers suitable for the purposes of this invention are nonionic surfactants alone or mixtures of nonionic and anionic surfactants. Suitable nonionic surfactants include the polyalkyleneoxy agents, e.g., polyethyleneoxy agents such as polyethyleneoxyethanol derivatives of methylene linked alkyl phenols, the ethylene glycol polyethers, the alkyl phenoxy polyethyleneoxyethanols having alkyl groups of 7 to 12 carbon atoms such as nonylphenoxypoly(ethyleneoxy)ethanols and condensation products of ethylene oxide with high alkyl mercaptans having alkyl groups of about 9 carbon atoms, and condensation products of ethylene oxide with alkyl thiophenols having alkyl groups of 6 to 15 carbon atoms; ethylene nonyl phenol polyethers; the fatty acid esters of polyhydric alcohols, e.g., propylene glycol fatty acid ester; and others set forth in Becher, Emulsions: Theory and Practice, 2nd Ed., Reinhold Publishing Corporation, New York, 221-225 (1965). Of the nonionic surfactants, the alkyl phenoxy polyethyleneoxyethanols having a hydrophilic moiety in the range from about 20 to about 60 ethyleneoxide units are preferred.

Anionic surfactants which may be suitably employed in combination with the nonionic surfactant include water soluble soaps of soap-forming monocarboxylic acids, e.g., alkali metal salts of linoleic acid dimer; and sulfated and sulfonated compounds having the general formula $R - O\ SO_3M$ and $R - SO_3M$, wherein R represents an organic radical having from 9 to 23 carbon atoms and M represents an alkali metal, an ammonium or amine group. Examples of the sulfonate and sulfate emulsifiers include sodium dodecyl benzene sulfonate, sodium oleyl sulfate, ammonium dodecyl benzene sulfonate, potassium lauryl sulfate, sodium dodecyl diphenyl oxide disulfonate, dioctyl potassium sulfosuccinate, dihexyl sodium sulfosuccinate, and the aryl sulfonate-formaldehyde condensation products.

Following addition of the emulsifier, the continuous addition of remaining monomer charge to to the polymerization zone is resumed and polymerization under similar conditions of time, temperature and catalyst set forth herein is continued. During the period of addition and polymerization of remaining monomer, it is sometimes desirable to charge the polymerization zone continuously or intermittently with a stream of catalyst and, if desired, a stream of base and/or activator. It is preferred to arrange the addition of catalyst, base and/or activator such that addition thereof continues for a short period, i.e., from about ½ to about 2 hours after addition of monomer is completed. During this period of uninterrupted polymerization (so-called final stage digestion), it is generally preferred to maintain the temperature of the resulting aqueous dispersion between about 70° to about 98°C to promote further conversion of monomer to polymer.

Before cooling, the aqueous dispersion of polymeric particles is commonly rendered increasingly alkaline by adjusting the pH to within the range of from about 6 to about 8. This may be done by adding ammonia or a water-soluble base, such as potassium or ammonium hydroxide, or a mixture thereof. Ammonium hydroxide, usually giving the best results in the least complicated way, is often preferred.

Having permitted the alkaline, aqueous dispersion to cool to ambient temperature, the aqueous dispersion of polymeric particles can be separated from undesirable impurities such as coagulum by-product, by filtering the aqueous dispersion of polymeric particles through a stainless steel filter having the filter surface perforated to correspond with the standard 16 mesh size of the U.S. Standard Sieve Series.

The filtered aqueous dispersion of polymeric particles prepared by the method described above and ordinarily containing from about 20 to about 60 weight percent, preferably from about 40 to about 50 weight percent, of non-film forming polymeric solids which form the polymeric pigment of this invention is ready to be combined with a detergent to provide the desired pigmented detergent.

For the purposes of this invention the term "detergent" means an aqueous liquid or semi-liquid detergent composition which contains water, a surface active agent and optionally one or more of such ingredients as a foam stabilizer, a foam booster or a hydrotrope such as an alcohol. Usually, the whole composition is adjusted to a neutral pH and as such is designated a light-duty liquid detergent. Also included within the term detergent are the so-called general purpose or heavy-duty liquid detergents which may contain in addition to the foregoing ingredients of the light-duty detergent one or more of the so-called alkaline boosters, such as alkali metal silicates, carbonates, polyphosphates and the like. Such aqueous liquid detergents are used extensively in dishwashing, laundering, bathing and in general purpose cleaning preparations. They frequently contain solubilizing aids (hydrotropes) such as sodium benzene sulfonate, sodium toluene sulfonate, sodium xylene sulfonate and/or alcohol. They are usually clear in appearance and have varying degrees of viscosity. The term detergent shall include so-called semi-liquid materials such as hair creams which contain in addition to the foregoing ingredients a substantial amount of thickener.

In the detergent, the aforementioned polymeric pigment is employed in an opacifying amount, preferably from about 0.2 to about 14 weight parts of pigment on a solids basis per 100 weight parts of surface active agent. When used, the alcohol or other hydrotrope is preferably present in amounts from about 1 to about 15 parts on the same basis with from about 2 parts to about 15 parts being especially preferred if the hydrotrope is alcohol. Expressed as percentages, one specific group of preferred detergent formulations may contain the following:

| Ingredient | Weight % |
|---|---|
| Surface Active Agent (including detergent, foam booster and/or foam stabilizer) | 20–60 |
| Alcohol | 1–10 |
| Hydrotrope (other than alcohol) | 0.5–10 |
| Water | 50–80 |
| Polymeric Pigment (35 to 50 percent solids) | 0.1–5 |

The following examples illustrate the invention, but are not to be construed as limiting its scope. Except as indicated, all parts and percentages are by weight.

EXAMPLE 1

Into a five-liter reaction vessel equipped with an agitator, reflux condenser, dropping funnels, thermometer, inert gas line, temperature control apparatus and temperature monitor is added 85 parts of water. After the water is heated to 90°C, an inert gas purge is begun and 0.5 parts of sodium persulfate is added. A continuous monomer stream consisting of 97 percent sytrene and 3 percent acrylic acid is begun at the constant rate of addition of about 22.2 parts per hour.

After about thirty minutes and approximately 11.1 parts of the monomers have been added, the monomer feed is stopped, and eight parts of a separate continuous addition stream consisting of 88 percent water and 12 percent sodium persulfate is begun at a continuous rate of 1.45 parts per hour.

After about fifteen minutes, an exothermic condition of the polymerization medium is observed to occur. At this time the monomer feed is resumed at the previously specified rate. After about three more hours of continuous addition of the monomer and catalyst solution streams, approximately 77.7 parts of the total 100 parts of monomers have been added to the reaction vessel. At this time, an emulsifier solution consisting of 10 parts water, 2 parts sodium dodecyl diphenyl ether disulfonate (90 percent active), 4 parts octylphenyl polyethoxy ethanol (70 percent active) and 0.2 parts sodium persulfate is added over a two to five minute period.

The monomer addition is continued at rate of about 22.2 parts per hour and is complete after about one more hour of continuous addition. The continuous addition stream of catalyst and water is finished about one hour and a half after the monomer feed is complete. The reaction mixture is digested for an additional hour at 82°C and cooled to ambient temperature with stirring. The resulting aqueous dispersion contains 48.3 percent polymer solids having an average particle diameter of 0.52 micron. A portion of the aqueous dispersion is withdrawn and tested for opacity. The remaining aqueous dispersion is combined with a commercial aqueous liquid detergent in the proportion of approximately 0.5–1 part of polymer solids per 100 parts of surfactant in the detergent. The resulting pigmented detergent is tested for stability. The results are recorded in Table I under Run No. 5.

EXAMPLE 2

For purposes of further illustration of the invention, the procedure of Example 1 is repeated several times with addition of the emulsifier solution at various times during polymerization. The resulting aqueous dispersions contain 46–50 percent polymer solids and have average particle diameters as shown in Table I. The resulting aqueous dispersions are similarly tested for opacity and then combined with the commercial aqueous detergent of Example 1 and are tested for stability. The results are recorded in Table I.

TABLE I

| Run No. | % Monomer Added Prior to Addition of Emulsifier | Average Particle Diameter(1), micron | Stability at 125°F(2) | Opacity (3) |
|---|---|---|---|---|
| 1 | 16.5 | 0.41 | Excellent | <2% |
| 2 | 33 | 0.42 | Excellent | " |
| 3 | 50 | Not Determined | Excellent | " |
| 4 | 67 | 0.43 | Excellent | " |
| 5 | 77.7 | 0.52 | Good | " |
| 6* | 90 | 0.43 | Poor | " |
| 7* | 99.5 | 0.56 | Poor | " |
| 8* | 99.9 | 0.56 | Poor | " |
| 9* | 100 | 0.49 | Poor | " |

*Not an example of this invention.
(1)Not more than about 5 weight percent of particles have diameters outside the range of 0.3 to 1.0 micron.
(2)Excellent = stable for more than 7 days, Good = stable for 7 days, and Poor = stable for less than 7 days.
(3)Percentage of light transmission at 0.01% polymer solids of aqueous dispersion as determined on Beckmann DB-GT Spectrometer at wavelength of 420 mμ.

What is claimed is:

1. A pigmented detergent containing (1) an aqueous liquid detergent comprising water and a surface active agent and (2) an opacifying amount of a non-film forming water- and detergent-insoluble emulsion polymer in the form of a latex, said latex being prepared by an emulsion polymerization process comprising the steps of (a) subjecting a polymerization recipe containing an aqueous medium, a catalyst and an incrementally added emulsion polymerizable ethylenically unsaturated monomer to conditions of emulsion polymerization; (b) adding an excess of a nonionic surfactant to the polymerization recipe when from about 15 to about 70 weight percent of the monomer has been polymerized and (c) continuing addition and emulsion polymerization of remaining monomer, said excess of nonionic surfactant being more than that required to completely cover the total surface area of the emulsion polymer particles of the latex.

2. The detergent of claim 1 wherein from about 2 to about 10 weight percent of nonionic surfactant based on the total emulsion polymerizable monomer is employed.

3. The detergent of claim 2 wherein the nonionic surfactant is a polyethyleneoxy agent.

4. The detergent of claim 3 wherein the polyethyleneoxy agent is an alkyl phenoxy polyethyleneoxyethanol having an alkyl group of 7 to 12 carbon atoms and a hydrophilic moiety in the range from about 20 to about 60 ethyleneoxide units.

5. The detergent of claim 1 wherein the emulsion polymerizable monomer is a hard monomer selected from the group consisting of monovinylidene carbocyclic aromatic monomers, hard esters of $\alpha,\beta$-ethylenically unsaturated esters of non-polymerizable carboxylic acids, $\alpha,\beta$-ethylenically unsaturated nitriles, and mixtures thereof with less than about 45 weight percent based on the resulting polymer of soft monomers selected from the group consisting of conjugated aliphatic dienes, alkyl acrylates, vinyl acetate and vinylidene chloride, and no greater than about 25 weight percent of $\alpha,\beta$-ethylenically unsaturated carboxylic acids.

6. The improvement of claim 5 wherein the detergent consists essentially of from about 20 to about 60 weight percent of surface active agent, from about 1 to about 10 weight percent of an alcohol, from about 0.5 to about 10 weight percent of a hydrotrope other than an alcohol, from about 0.1 to about 5 weight percent of the latex having from about 35 to about 50 weight percent solids and a remaining amount of water.

7. The improvement of claim 6 wherein the polymer of the latex is a styrene/acrylic acid copolymer which is present in an amount of approximately 0.5 to 1 part of polymer solids per 100 parts of the surface active agent.

8. The pigmented detergent of claim 1 wherein the emulsion polymer is a copolymer of from about 50 to about 99 weight percent of monovinylidene carbocyclic aromatic monomer, from about 0 to about 49 weight percent of $\alpha,\beta$-ethylenically unsaturated nitrile and from about 1 to about 5 weight percent of an $\alpha,\beta$-ethylenically unsaturated carboxylic acid.

9. The pigmented detergent of claim 8 wherein the amount of the latex is from about 0.2 to about 14 weight parts of latex polymer solids per 100 weight parts of detergent.

10. The detergent of claim 1 wherein no more than about 5 percent of the particles of the resulting latex are outside the range of from 0.2 to 2 microns.

* * * * *